United States Patent [19]
Taylor et al.

[11] Patent Number: 6,139,523
[45] Date of Patent: Oct. 31, 2000

[54] ISOLATION SYSTEM FOR PRESSURE GAUGES FOR PERMITTING REPEATED USE WITHOUT STERILIZATION

[75] Inventors: Steven R. Taylor, Salt Lake City; Arlin Dale Nelson, Sandy, both of Utah

[73] Assignee: Merit Medical Systems, Inc., South Jordan, Utah

[21] Appl. No.: 09/241,624

[22] Filed: Feb. 1, 1999

[51] Int. Cl.[7] ................................................. A61M 29/00
[52] U.S. Cl. .................................. 604/98.01; 604/98.01; 604/100
[58] Field of Search ............................. 604/97–100, 121, 604/118, 246; 73/715

[56] References Cited

U.S. PATENT DOCUMENTS

| | | | |
|---|---|---|---|
| 3,890,842 | 6/1975 | Ramsey, III | 73/420 |
| 4,655,749 | 4/1987 | Fischione | 604/98 |
| 5,057,078 | 10/1991 | Foote et al. | 604/99 |
| 5,163,904 | 11/1992 | Lampropoulos et al. | 604/100 |
| 5,449,345 | 9/1995 | Taylor et al. | 604/100 |
| 5,472,424 | 12/1995 | Lampropoulos et al. | 604/99 |
| 5,752,935 | 5/1998 | Robinson et al. | 604/97 |

*Primary Examiner*—Wynn Wood Coggins
*Assistant Examiner*—Kevin C. Sirmons
*Attorney, Agent, or Firm*—Workman, Nydegger, Seeley

[57] ABSTRACT

Systems and methods for isolating a pressure gauge from sources of potential contamination so that the pressure gauge may be reused in multiple medical procedures without having to be subjected to a sterilization procedure. The systems of the invention may include a syringe assembly having a pressure gauge removably attached to a syringe. The pressure gauge is isolated from sources of potential contamination in at least two ways. First, a flexible membrane separates a pressure transducer diaphragm of the pressure gauge from the pressurized fluid of the syringe. The flexible membrane prevents the pressure gauge from contacting the fluid and transmits pressure and forces from the fluid to the pressure gauge. Second, a substantially transparent disposable bag or film covers surfaces of the pressure gauge that would be otherwise exposed to human contact or other contaminants. During medical procedures, the pressure gauge maintains its sterile condition. After use, the pressure gauge may be removed from the syringe and subsequently used with a second syringe without an intervening sterilization procedure. The syringe assemblies may further include a balloon-tipped catheter for use in angioplasty and related medical procedures.

25 Claims, 3 Drawing Sheets

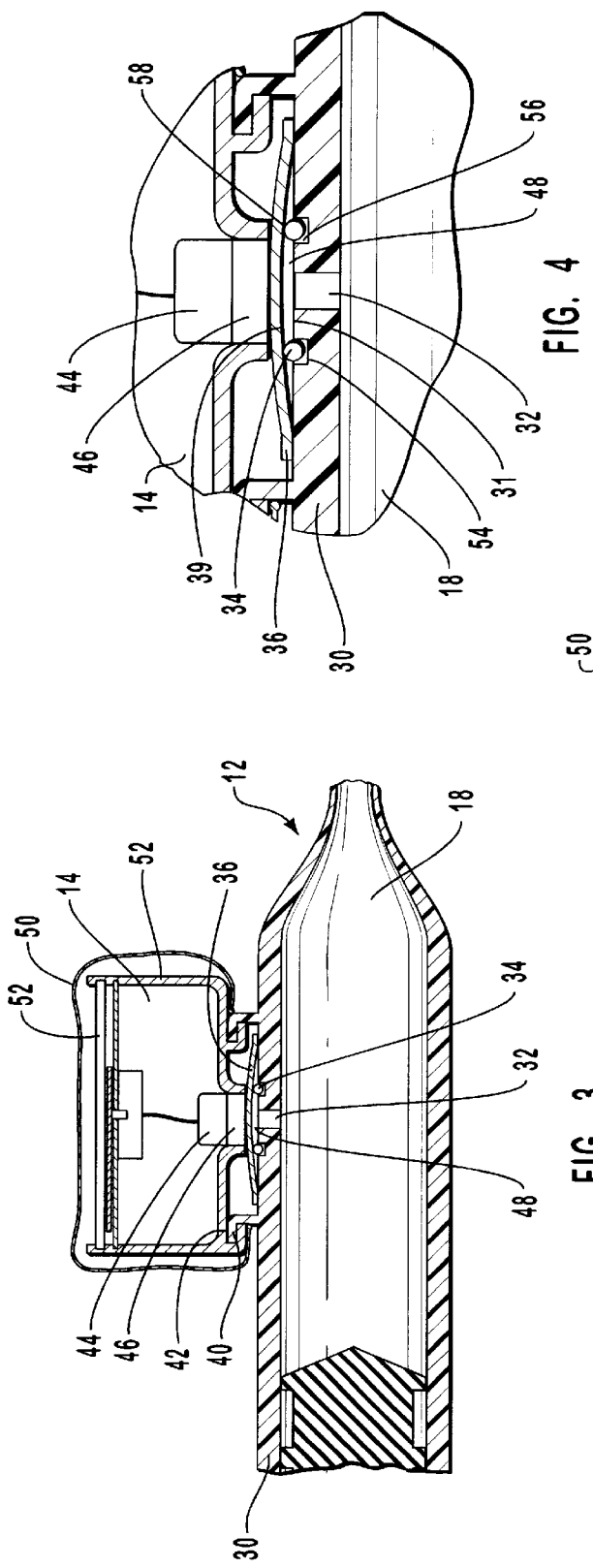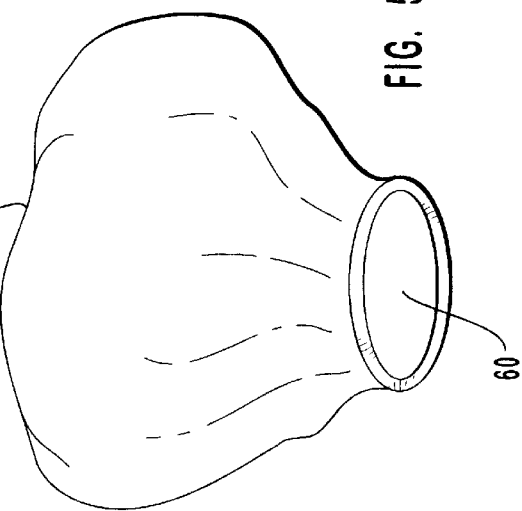

ISOLATION SYSTEM FOR PRESSURE GAUGES FOR PERMITTING REPEATED USE WITHOUT STERILIZATION

BACKGROUND OF THE INVENTION

1. The Field of the Invention

The present invention relates to pressure gauges for monitoring fluid pressure generated in a syringe during a medical procedure such as angioplasty. More particularly, the present invention relates pressure gauges that are isolated from potential sources of contamination so as to be repeatedly used in medical procedures without being sterilized between uses.

2. Relevant Technology

In recent years, balloon-tipped catheters have become increasingly useful in various medical procedures. For example, balloon-tipped catheters have been used to reduce the intrusiveness of medical procedures in various fields of medicine, such as urology, gynecology, cardiology, and the like. Particularly in the treatment of coronary artery disease, the use of balloon-tipped catheters and their associated fluid pressurization systems has become widespread.

Coronary artery disease is the narrowing of the arteries that feed oxygen-rich blood to the heart. The heart needs adequate amounts of oxygen to continually and efficiently pump blood throughout the body. When arteries leading to the heart become narrowed and constricted due to coronary artery disease, several problems can develop. A person with coronary artery disease can experience angina, which is characterized by chest pain or pressure that radiates to the aim or jaw and is caused by a lack of oxygen-rich blood to the heart muscle. If untreated, coronary artery disease can lead to or contribute to heart failure and death.

In recent years, coronary angioplasty has become a common and accepted alternative to the vastly more intrusive coronary bypass surgery. Coronary bypass surgery involves surgical access to the heart, placing the patient on an extracorporeal blood oxygenation system so that the heart can be stopped for surgery, and then surgically attaching one or more passageways by which blood can bypass a clogged coronary artery, all under general anesthesia. Coronary angioplasty, which can be performed using a local anesthetic, involves running a dilation or "balloon-type" catheter to the diseased artery and then inflating the balloon in order to compress plaque within the artery, thereby obtaining increased blood flow to the heart. Compared to coronary bypass surgery, coronary angioplasty is less intrusive and traumatic, typically involves less risk to the patient, and significantly reduces the patient's discomfort and recovery time.

During inflation of the balloon during angioplasty, no blood can flow through the artery that is being mechanically dilated. The disruption of blood flow must be limited in duration to about 20 to 60 seconds, so as to avoid tissue damage due to oxygen deprivation. Hence, it is important to carefully monitor the inflation pressure and duration to ensure that blood flow is restored before tissue damage can occur. In most cases, it is not possible to adequately dilate a diseased artery in a single inflation. In cases where it is necessary to undertake multiple inflations in the same artery, it is important to allow sufficient time between successive inflations so that the tissues fed by the diseased artery can become fully oxygenated before blood flow is disrupted again. At the same time, a successful angioplasty procedure requires that the dilation of the artery be conducted for a significant period of time.

Various devices and gauges have been developed for monitoring inflation and deflation of balloon tipped catheters during angioplasty. A typical pressure gauge of the prior art has a pressure transducer diaphragm that is in direct fluid contact with the inflation fluid within the inflation syringe. For example, the pressure gauge is directly mounted on the exterior of the syringe barrel over a port extending through the barrel. As fluid pressure is generated within the inflation syringe, the fluid pressure is transmitted through the port to the pressure transducer diaphragm. The pressure gauge senses the fluid pressure and displays or records the magnitude of the fluid pressure in analog or digital form.

In order to maintain a sterile environment during the angioplasty procedure, several techniques have been developed with respect to pressure gauges and methods of sensing fluid pressure. It can be understood that as the pressure transducer diaphragm is exposed to inflation fluid, the pressure gauge is subject to possible contamination. Moreover, the exposed surfaces of the pressure gauge, such as the housing and a display window through which the measurement readings are displayed, may be exposed to other contaminants during use. For example, medical personnel sometimes touch the pressure gauge during normal use and fluids may be splashed onto pressure gauge surfaces. Although pressure gauges and the inflation fluid ordinarily do not contact the patient's tissue or bodily fluids, it is important that the pressure gauges be sterile for safety reasons. Using a pressure gauge that has previously been contaminated by inflation fluid or contact with other contaminants without subjecting it to a sterilization procedure has been unacceptable according to current medical practice.

One method for providing sterile pressure gauges is to use a new device for each angioplasty or other medical procedure. According to this method, the pressure gauges are one-use devices that are discarded after one medical procedure. Disposable pressure gauges ensure that each angioplasty is performed with a sterile pressure gauge. However, the use of disposable pressure gauges adds significant cost to each operation.

Alternatively, other pressure gauges are designed to be sterilized after being used in a medical procedure, and are thereby reusable. For example, sterilization may be conducted thermally in an autoclave or chemically by applying a sterilizing chemistry to the pressure gauge. Typically, such sterilizable pressure gauges have surfaces of stainless steel or another sterilizable material. Examples of sterilizable and reusable pressure gauges are disclosed in copending U.S. patent application Ser. No. 09/048,091, filed Mar. 25, 1998, entitled "Pressure Gauge with Digital Stepping Motor and Reusable Transfer Plug." For purposes of disclosure, the foregoing patent application is incorporated herein by specific reference. Sterilizable pressure gauges represent a significant advancement in the art, since the cost of a new pressure gauge is not included in each medical procedure.

Either of the foregoing two methods are adequate for providing sterile pressure gauges in many situations. However, it can be understood that it would be a fixer advancement in the art to provide pressure gauges that are both reusable and do not need to be sterilized between uses. Pressure gauges that may be used multiple times without intervening sterilization procedures would significantly reduce the cost and effort now required for providing sterile pressure gauges. In particular, the cost associated with the time and equipment for sterilizing reusable pressure gauges could be avoided. In addition, such pressure gauges would eliminate the cost of using a new, one-use pressure gauge for each medical procedure.

SUMMARY OF THE INVENTION

The present invention relates to pressure gauges that are reusable in multiple medical procedures and that do not need to be sterilized between uses. The pressure gauges are configured for use with inflation syringes in a wide range of medical procedures, including angioplasty and related operations. To ensure that the pressure gauges of the invention are sterile during the multiple medical procedures, the pressure gauges are isolated from the environment and potential contaminants in at least two ways. First, a flexible membrane disposed between the inflation fluid and the pressure gauge isolates the pressure transducer diaphragm from direct contact with the inflation fluid in the syringe. Second, a transparent plastic bag or film covers the surfaces that would be otherwise exposed in order to prevent medical personnel or other sources of contamination from contacting the pressure gauge.

In one implementation of the invention, the pressure gauge is included in a syringe assembly. The pressure gauge is mounted on the barrel of an inflation syringe to detect the pressure generated by inflation fluid within the syringe. A catheter, which may be balloon-tipped, is in fluid communication with the inflation fluid by being attached to the distal end of the inflation syringe. The inflation syringe has a plunger slidably disposed within the syringe barrel. Advancement of the plunger through the barrel forces inflation fluid from the barrel into the catheter. When the syringe is used in combination with a balloon-tipped catheter, the inflation fluid forced into the catheter causes inflation of the balloon and a corresponding increase in fluid pressure.

In this implementation, a port extends through the sidewall of the barrel and permits fluid communication between the syringe and a pressure chamber disposed on the outer surface of the barrel. The pressure chamber is enclosed by a flexible membrane bonded to the outer surface of the barrel over the port. The pressure gauge is rigidly and removably attached to the outer surface of the syringe barrel such that a pressure transducer diaphragm of the pressure gauge is in direct contact with the flexible membrane. As pressure is generated within the syringe, the pressure is communicated through the port and to the pressure chamber. Since the flexible membrane is in contact with the pressure gauge, force associated with the generated fluid pressure is transmitted through the membrane to the pressure transducer diaphragm. In this manner, the pressure gauge senses and detects the fluid pressure within the syringe without being in direct fluid contact with the inflation fluid. Moreover, the flexible membrane isolates the pressure gauge from the inflation fluid, thereby preventing the inflation fluid from contaminating the pressure gauge.

According to one aspect of the present invention, an O-ring circumscribes the port and is disposed between the outer surface of the barrel and the flexible membrane. The O-ring facilitates the transmission of force from the pressurized fluid in the pressure chamber to the pressure gauge. In particular, the O-ring supports the flexible membrane and prevents it from collapsing against the outer surface of the barrel. This configuration maintains the patency of the pressure chamber and provides adequate contact between the pressure gauge and the flexible membrane, even if vacuum pressure is experienced.

According to this implementation, a disposable transparent film or bag covers surfaces of the pressure gauge that would otherwise be exposed. For example, the film may be a polypropylene bag having an elastic opening to securely stretch over and remain positioned on the pressure gauge. The film prevents potential contamination of the surfaces of the pressure gauge. For example, medical personnel may touch and handle the pressure gauge through the film without contaminating the pressure gauge surfaces.

A pressure gauge of the invention may be used in multiple medical procedures by first removably attaching it to an inflation syringe according to the configuration described above. Next, the film or bag is applied to the pressure gauge to cover the otherwise exposed surfaces. The medical operation proceeds as usual, while the pressure gauge is used to monitor the fluid pressure generated in the inflation syringe. While the pressure gauge is attached to the inflation syringe, the flexible membrane isolates the pressure gauge from direct contact with the inflation fluid. Moreover, the film or bag prevents contamination of the surfaces of the pressure gauge.

After the medical procedure is completed, the pressure gauge is removed from the inflation syringe, and the film and the inflation syringe may be discarded. The pressure gauge remains in the same sterile condition as before the medical procedure. As desired, the pressure gauge may again be removably attached to a new inflation syringe and used in another medical procedure. A significant advantage of the pressure gauges and the methods of the invention is that the pressure gauge does not need to be subjected to a sterilization procedure between uses, but instead maintains a medically-acceptable level of sterilization during repeated uses.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 3 is a partial cross-sectional view of the syringe assembly of FIG. 2, further illustrating a pressure gauge removably attached to the inflation syringe and a disposable film covering the pressure gauge.

FIG. 4 is an enlarged partial cross-sectional view of the pressure chamber and surrounding structures of the syringe assembly of FIG. 3.

FIG. 5 is a perspective view of the disposable film of FIG. 3.

DETAILED DESCRIPTION OF THE PREFERRED EMBODIMENTS

The present invention relates to pressure gauges that are reusable in multiple medical procedures and that do not need to be sterilized between uses. The invention further extends to syringe assemblies wherein a pressure gauge is removably attached to a syringe and is isolated from potential sources of contamination such as fluid within the syringe and contact with medical personnel or other contaminates.

The pressure gauges are configured for use with syringes in a wide range of medical procedures, including angioplasty and related operations. To ensure that the pressure gauges of the invention are sterile during the multiple medical procedures, the pressure gauges are isolated from the environment and potential contaminants in at least two ways. First, the pressure transducer diaphragm is isolated from direct contact with the fluid in the syringe by a flexible membrane disposed between the fluid and the pressure gauge. Second, a disposable covering, such as a transparent plastic bag or film, covers surfaces that would be otherwise exposed in order to prevent medical personnel or other sources of contamination from contacting the pressure gauge.

The invention may be best understood by referring to FIGS. 1–5, which illustrate the elements, features, and operation of one embodiment of the invention. In the embodiment that is primarily discussed herein, the syringe assembly is configured for use in angioplasty or other medical procedures in which the syringe is used to supply inflation pressure to a dilation catheter. While this is one presently preferred embodiment, it is to be understood that the broad principles taught herein may be applied to other medical devices that generate or experience fluid pressure. Furthermore, the invention is applicable to many types of medical procedures in which it is desirable to monitor fluid pressure using a pressure gauge in a sterile condition. Accordingly, the present invention is should not be limited to the specific embodiments disclosed in detail herein.

Figure 1:
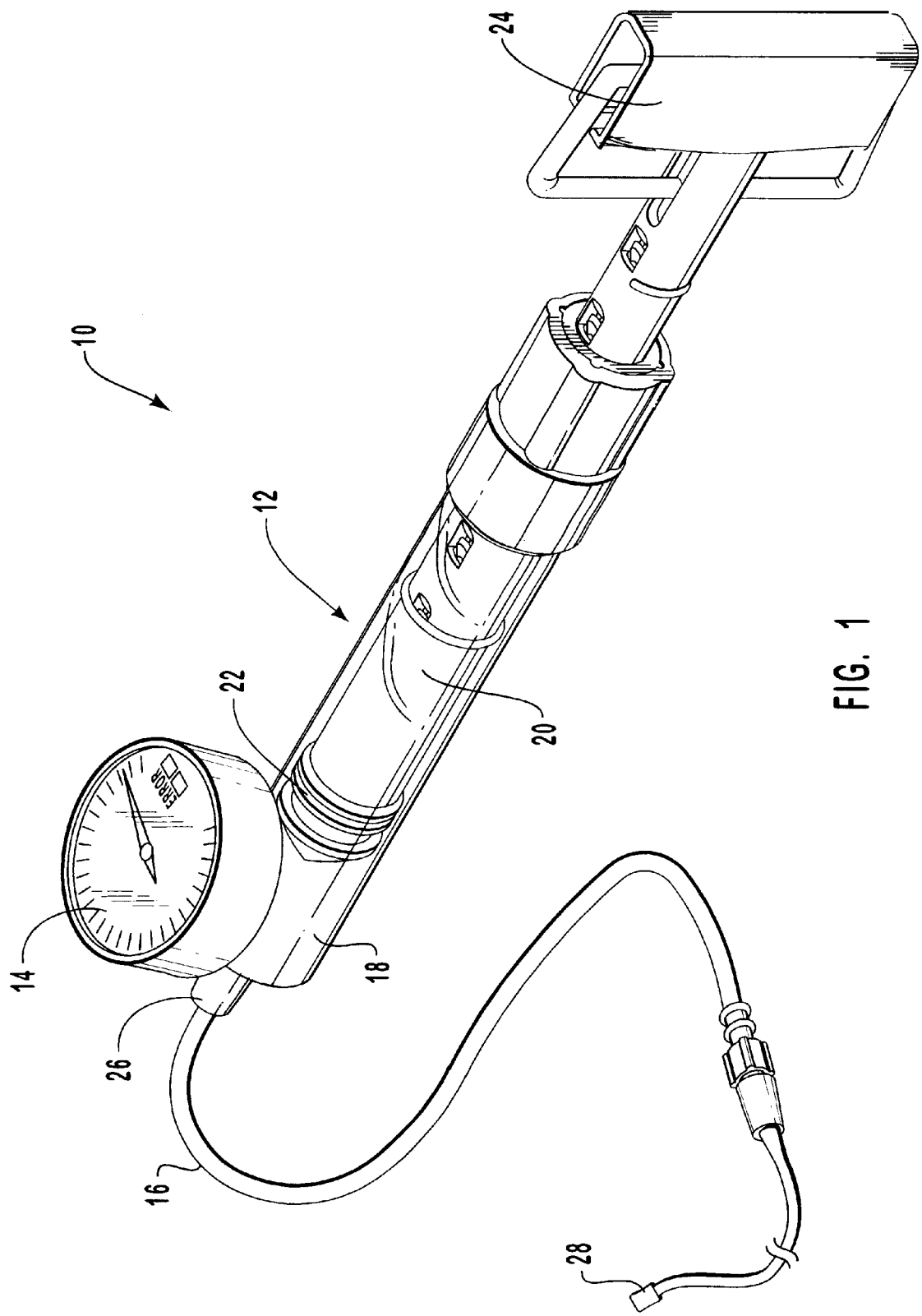
FIG. 1 is a perspective view of a syringe assembly according to the invention, wherein a pressure gauge is mounted on an inflation syringe.

Referring first to FIG. 1, one presently preferred embodiment of a syringe assembly is illustrated. Syringe assembly 10 includes a syringe 12, pressure gauge 14, and a catheter assembly 16, and is configured to be used in angioplasty or other related procedures. Syringe 12 includes a hollow barrel 18 and a plunger 20 slidably disposed within the barrel. A plug 22 is positioned at the distal end of plunger 20 to sealingly engage barrel 18 as the plunger is advanced and retracted through the barrel. A handle 24 of any convenient shape is located at the proximal end of plunger 20. A physician grasps handle 24 and advances plunger 20 through barrel 18, thereby expelling fluid from the barrel into catheter assembly 16.

In this embodiment, catheter assembly 16 is in fluid communication with syringe 12 by means of an opening 26 at the distal end of barrel 18. A balloon 28 may be positioned at the distal end of the catheter assembly 16 for use in angioplasty or other related medical procedures. As fluid is expelled from syringe 12 into catheter assembly 16, the pressure of the fluid generally increases and balloon 28 inflates. When used in angioplasty, the inflated balloon 28 may be used to radially compress plaque deposits within diseased arteries. Pressure gauge 14 visually displays the magnitude of the fluid pressure within syringe 12. As inflation of balloon 28 continues, the operating physician may monitor the generated fluid pressure by referring to pressure gauge 14. Thus, pressure gauge 14 is one example of pressure monitoring means for detecting fluid pressure generated within the barrel of the syringe.

Syringes similar to the one illustrated in FIG. 1 are more particularly described in U.S. Pat. Nos. 5,449,344 to Taylor et al. and 5,135,488 to Foote et al., which are incorporated herein by reference for purposes of disclosure. However, it is to be understood that the nature and mechanical aspects of syringe 12 are not limited to those specific features illustrated in FIG. 1 or disclosed in the foregoing patents, and that a variety of different types of syringe designs could be utilized without departing from the spirit and scope of the present invention. Indeed, the pressure gauges disclosed herein may be adapted to measure fluid pressures generated within devices other than syringes. In these cases, the pressure gauge is adapted to be respond to another fluid system in which a fluid pressure may be generated.

Pressure gauge 14 is isolated from the fluid within syringe 12 in order to maintain the sterile condition of the pressure gauge and to allow the pressure gauge to be used in multiple medial procedures without intervening sterilization. In general, the pressure gauges of the invention remain isolated from the fluid by a flexible membrane or bladder that transmits forces from the fluid to the pressure gauge. Such flexible membranes or bladders are examples of diaphragm means for communicating fluid pressure in the syringe to the pressure gauge and for isolating the pressure gauge from direct contact with the fluid.

Figure 2:
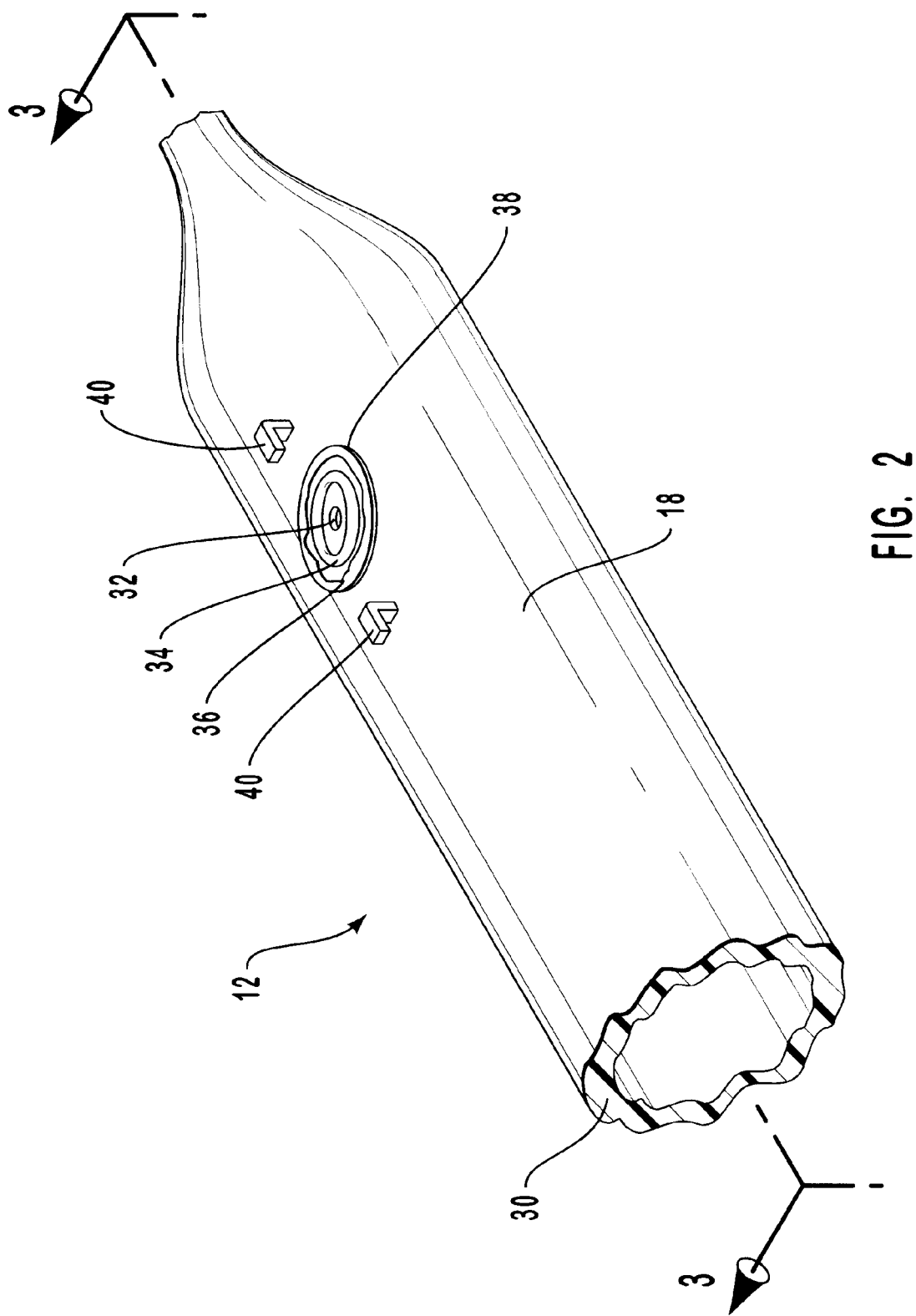
FIG. 2 is a cutaway perspective view of a portion of a syringe assembly according to the invention, depicting a port extending through a sidewall of a syringe barrel, an O-ring circumscribing the port, and a flexible membrane covering the port.

FIG. 2 further illustrates syringe assembly 10 of FIG. 1, including a flexible membrane for transmitting forces to the pressure gauge. Barrel 18 has a sidewall 30 with a port 32 extending therethrough. In this embodiment of the invention, an O-ring 34 concentrically surrounds port 32 and is disposed on the outer surface of sidewall 30. Although the invention may be practiced in the absence of O-ring 34, its presence provides several advantages that are discussed herein. O-ring 34 may be formed, for example, from any suitable, pliant polymeric material.

A flexible membrane 36 (shown in cutaway in FIG. 2) is also positioned on the outer surface of sidewall 30 and covers port 32 and is one example of the diaphragm means. Flexible membrane 36 may be formed from any material that is sufficiently flexible to transmit forces from the fluid to the pressure gauge and tough enough to withstand tearing, bursting, or otherwise failing in response to the pressures and forces that the membrane experiences during use. For example, a presently preferred flexible membrane 36 comprises a film formed from a polyester material, such as Mylar. Flexible membrane 36 is preferably joined to the outer surface of sidewall 30 in a fluid-tight manner by, for example, an ultrasonic or another bonding technique at or near periphery 38 of the flexible membrane. Accordingly, the interface at which flexible membrane 38 is bonded to the outer surface of sidewall 30 constitutes one example of sealing means for joining the flexible membrane and the syringe in a fluid-tight manner.

The syringe assembly preferably includes attachment means for removably attaching the pressure gauge to the syringe assembly. Hooks 40 or other male components formed on sidewall 30 are one example of the attachment means. In general, the attachment means may be any structure for rigidly securing the pressure gauge to the syringe assembly so as to resist displacement of the pressure gauge away from the syringe assembly as force is transferred from the flexible membrane to the pressure gauge. Furthermore, the attachment means generally allows the pressure gauge to be removed from the syringe assembly after use so that the pressure gauge may be reused with another syringe assembly. Turning to FIG. 3, the manner in which hooks 40 secure the pressure gauge may be further understood. Pressure gauge 14 includes slots 42 that matingly engage hooks 40, thereby securing the pressure gauge to the syringe assembly. Alternatively, the attachment means may include female components such as grooves, slots, or the like, that mate with corresponding structures on the pressure gauge. In another embodiment, the attachment means may comprise a threaded well formed about periphery 38 of flexible membrane 36, and which mates with a corresponding threaded neck on the pressure gauge.

As shown in FIG. 3, pressure gauge 14 includes a pressure transducer 44 having a diaphragm 46. In order for pressure gauge 14 to reliably sense the generated fluid pressure, diaphragm 46 is situated in direct contact with flexible membrane 36. In one embodiment, flexible membrane 36 may be biased against diaphragm 46 when the pressure within syringe barrel 18 is neutral with respect to the atmospheric pressure. The resilient properties of O-ring 34 facilitate the biased contact of flexible membrane 36 against diaphragm 46 and maintain such contact through a wide range of fluid pressures.

Pressure gauge 14 and other structures that correspond to the pressure monitoring means may be substantially any mechanical or electronic device that senses forces transmitted through flexible diaphragm 36 and displays and/or records the magnitude of the sensed fluid pressure. One example of a suitable pressure gauge is disclosed in U.S. patent application Ser. No. 09/048,091, filed Mar. 25, 1998, entitled "Pressure Gauge with Digital Stepping Motor and Reusable Transfer Plug." However, since the surface of the pressure gauges are isolated from potential contaminants in the environment, it can be understood that the specific structure, elements, and method of operation of the pressure gauges used with the invention are not critical. Furthermore, while the components of some pressure gauges have been limited to those that are able to withstand thermal or chemical sterilization procedures, such limitations are not present with respect to the pressure gauges of the invention. Accordingly, the pressure transducers, the power supplies, the display devices, and the other components included in the pressure gauges used with the invention need not be selected according to considerations regarding their compatibility with high temperature or chemical environments.

FIG. 3 and the enlarged view of FIG. 4 further illustrate the manner in which pressure and forces are communicated between barrel 18 and pressure transducer diaphragm 46. As discussed above, positive fluid pressure with respect to atmospheric pressure is generated when the plunger of the syringe assembly is advanced into barrel 18. Port 32, extending through sidewall 30, establishes fluid communication between barrel 18 and a pressure chamber 48 situated at the outer surface of sidewall 30. Fluid generally fills pressure chamber 48 such that the pressure generated within barrel 18 is substantially the same as the pressure within pressure chamber 48. Pressure chamber 48 is defined by the inner surface 39 of flexible membrane 38, the outer surface 31 of sidewall 30, and O-ring 34, as shown in FIG. 4.

As further illustrated in FIG. 4, O-ring 34 may be seated in an annular groove 54 formed into sidewall 30. O-ring 34 establishes a first fluid-tight seal 56 between itself and sidewall 30 and further establishes a second fluid-tight seal 58 between itself and flexible membrane 36. Fluid-tight seals 56 and 58 substantially prevent pressurized fluid from escaping from pressure chamber 48 into the surroundings. In view of the foregoing, O-ring 34 constitutes a further example of sealing means for joining flexible membrane 38 and syringe 12 in a fluid-tight manner. Moreover, O-ring 34 and fluid-tight seals 56 and 58 relieve much of the stress that would otherwise bear on the bonded interface between flexible membrane 38 and the outer surface of sidewall 30. As a result, the inclusion of O-ring 34 allows the interface between flexible membrane 38 and sidewall 30 to be smaller, the minimum strength of the bond at the interface to be less, and the diameter of the flexible membrane to be smaller than would otherwise be required. However, the invention may be practiced in the absence of O-ring 34, in which case the bond at the interface between flexible membrane 38 and the outer surface of sidewall 30 should be sufficiently strong to prevent the fluid pressure from breaking the bond.

As positive fluid pressure is generated within barrel 18 and pressure chamber 48, the fluid exerts force on flexible membrane 36, which responds by transmitting the force to pressure transducer diaphragm 46. Thus, when the fluid pressure increases, the force transmitted to pressure transducer diaphragm 46 likewise increases. In some situations, syringe assembly 12 may be used to generate a negative fluid pressure relative to atmospheric pressure by, for example, retracting the plunger part way through barrel 18. In this case, the negative pressure is communicated to pressure chamber 48. In response to the negative pressure, flexible membrane 36 tends to deflect downward, thereby reducing the volume of pressure chamber 48. O-ring 34 prevents flexible membrane 36 from fully collapsing inwardly and closing the pressure chamber 48 and tends to maintain the contact between the flexible membrane and diaphragm 46 during negative pressure conditions. Thus, this embodiment of the syringe assemblies of the invention allows pressure gauge 14 to detect negative pressures generated within the syringe.

FIGS. 3 and 5 further illustrate disposable transparent bag 50 that covers the otherwise exposed surfaces 52 of pressure gauge 14. Bag 50 and other substantially transparent films represent examples of covering means for protecting the pressure gauge from contamination during use of the syringe assembly in a medical procedure. One preferred material for use in bag 50 is polypropylene, although a variety of other polymeric materials are also suitable. Because of the substantially transparent nature of bag 50, pressure gauge 14 may be visually monitored by the operating physician or other medical personnel during medical procedures. A preferred embodiment of bag 50 has an elastic or other resilient opening 60 that tends to close in around the base of pressure gauge 14 when applied thereto. Accordingly, when bag 50 covers pressure gauge 14, the bag is reliably secured over the pressure gauge and substantially resists inadvertently falling off during use. It can also be understood that bag 50 is relatively very inexpensive such that the savings gained by reusing the pressure gauges of the invention in multiple medical procedures, while eliminating the need for intervening sterilization operations, far outweigh the cost of the bags.

Methods for using the pressure gauges and syringe assemblies of the invention to perform multiple medical procedures may also be described by making reference to FIG. 3. In a first step, there is provided a pressure gauge 14 in a sterile condition sufficient for medical use. Pressure gauge 14 is then removably and rigidly attached to syringe assembly 12 as described herein. The transparent bag 50 may be stretched over pressure gauge 14 before it is attached to syringe assembly 12 in order to allow the pressure gauge to be handled by medical personnel without directly contacting pressure gauge surfaces. Alternatively, bag 50 may be applied to pressure gauge 14 after the pressure gauge has been attached to syringe assembly 12. Depending on the particular pressure gauge 14, a zeroing operation may be conducted to initialize the pressure reading with respect to the particular syringe assembly 12. With pressure gauge 14 in its desired position on syringe assembly 12, the angioplasty or other medical procedure is then performed as desired. It is noted that pressure gauge 14 responds from the standpoint of the operating physician in a substantially similar manner as pressure gauges attached to a syringe according to a conventional configuration. In particular, pressure gauge 14 responds to fluid pressure generated within syringe 12 and displays and/or records the magnitude of the fluid pressure.

After the medical procedure has been completed, pressure gauge 14 is removed from syringe assembly 12. Pressure gauge 14 is withdrawn from bag 50 and both syringe 12 and bag 50 may be discarded. During the medical procedure, bag 50 prevents potential contaminants from contacting surfaces 52, while flexible membrane 36 isolates diaphragm 46 from the fluid of the syringe assembly. Accordingly, pressure gauge 14 has not been contaminated during the previous medical procedure and remains in the same sterile condition as before being used. In this sterile condition, pressure gauge 14 may be reused in combination with a new syringe 12 and a new bag 50 in a subsequent medical procedure. Pressure gauges may be repeatedly used an indefinite number of times according to the systems and methods of the invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A syringe assembly for generating fluid pressure, comprising:

a syringe having a barrel and a plunger slidably disposed within said barrel;

a port extending through a sidewall of said barrel;

pressure monitoring means for detecting fluid pressure generated within said barrel;

an essentially flat, flexible diaphragm means, situated between said port and said pressure monitoring means, for communicating pressure of a fluid in said syringe to said pressure monitoring means and for isolating said pressure monitoring means from direct contact with said fluid;

sealing means for joining said diaphragm means and said syringe in a fluid-tight manner; and covering means for protecting said pressure monitoring means from contamination during use of said syringe assembly in a medical procedure, said pressure monitoring means being reusable without being subjected to a sterilization procedure.

2. A syringe assembly as defined in claim 1, wherein said covering means comprises a substantially transparent disposable film.

3. A syringe assembly as defined in claim 1, wherein said sealing means comprises an O-ring in contact with said diaphragm means and said sidewall of said barrel, said O-ring circumscribing said port.

4. A syringe assembly as defined in claim 1, wherein said sealing means comprises an interface between a flexible membrane and said sidewall of said barrel.

5. A syringe assembly as defined in claim 1, further comprising a balloon-tipped catheter extending distally from an opening at a distal end of said syringe.

6. A syringe assembly as defined in claim 1, wherein said pressure monitoring means comprises a pressure gauge having a pressure transducer in contact with said diaphragm means.

7. A syringe assembly as defined in claim 1, wherein said diaphragm means comprises a flexible membrane extending over said port and being joined to said sidewall of said barrel at an interface circumscribing said port.

8. A syringe assembly as defined in claim 7, further comprising a pressure chamber defined by an inner surface of said flexible membrane, an outer surface of said sidewall, and an O-ring circumscribing said port, fluid communication being established through said port between said pressure chamber and said barrel.

9. A syringe assembly as defined in claim 1, further comprising attachment means for removably attaching said pressure monitoring means to said sidewall of said barrel.

10. A syringe assembly for generating fluid pressure, comprising:

a syringe having a barrel and a plunger slidably disposed in said barrel;

a port extending through a sidewall of said barrel;

an essentially thin, flat flexible membrane extending over said port so as to cover said port in a sheet-like fashion, said flexible membrane being joined to said sidewall;

a pressure chamber defined by an inner surface of said membrane and an outer surface of said sidewall, said port establishing fluid communication between said pressure chamber and said barrel such that fluid pressure generated in said barrel is also generated in said pressure chamber;

a pressure gauge removably attached to said barrel, said pressure gauge having a pressure transducer disposed against said flexible membrane, wherein force associated with said fluid pressure is transmitted through said flexible membrane to said pressure transducer in a sheet-like fashion; and a disposable covering extending over said pressure gauge, said disposable covering and said membrane substantially isolating said pressure gauge from contamination, said pressure gauge being reusable in multiple medical procedures without being subjected to a sterilization procedure.

11. In a system wherein a pressure gauge removably attached to a syringe is used to monitor fluid pressure generated within the syringe, a method for maintaining the pressure gauge in a sterile condition and reusing the pressure gauge in multiple medical procedures, the method comprising the steps of:

during a first medical procedure wherein fluid pressure is generated within a first syringe, isolating said pressure gauge from contaminants, including the steps of:

using an essentially thin, flat, flexible membrane that extends and covers a port in said syringe in a sheet-like fashion and which is in contact with a pressure transducer of said pressure gauge to communicate said fluid pressure to said pressure gauge and to prevent fluid within said first syringe from contacting said pressure gauge in a sheet-like fashion; and using a disposable covering extending over said pressure gauge to prevent contamination of surfaces of said pressure gauge;

after said first medical procedure, removing said pressure gauge from said first syringe;

removing said disposable covering from said pressure gauge;

without sterilizing said pressure gauge, attaching said pressure gauge to a second syringe; and monitoring fluid pressure generated in said second syringe during a second medical procedure using said pressure gauge.

12. A syringe assembly as defined in claim 10, wherein said flexible membrane is a polyester film.

13. A syringe assembly as defined in claim 10, wherein said pressure transducer is disposed against said flexible membrane in a manner so as to be capable of sensing both positive fluid pressure and negative fluid pressure with respect to atmospheric pressure.

14. A syringe assembly as defined in claim 10, further comprising an O-ring disposed on said outer surface of said sidewall and circumscribing said port.

15. A syringe assembly as defined in claim 10, further comprising a balloon-tipped catheter extending distally from an opening at a distal end of said syringe.

16. A syringe assembly for generating fluid pressure, comprising:

a syringe having a barrel, a plunger slidably disposed in said barrel, and a port extending through a sidewall of said barrel;

a flexible membrane extending over said port, said membrane being joined to said sidewall at an interface that circumscribes said port;

an O-ring disposed between said flexible membrane and said sidewall of said barrel, said O-ring circumscribing said port between said port and said interface;

a first fluid-tight seal between said sidewall and said O-ring;

a second fluid tight seal between said flexible membrane and said O-ring;

a pressure chamber defined by an inner surface of said membrane, an outer surface of said sidewall, and said O-ring, fluid communication being established through said port between said pressure chamber and said barrel;

a pressure gauge removably attached to said barrel, said pressure gauge having a pressure transducer disposed against said flexible membrane; and a disposable covering extending over said pressure gauge, said disposable covering and said membrane substantially isolating said pressure gauge from contamination.

17. A syringe assembly as defined in claim 16, further comprising an annular groove formed into an outer surface of said sidewall, said O-ring being seated in said annular groove.

18. A syringe assembly as defined in claim 16, wherein said disposable covering comprises a substantially transparent polymeric film.

19. In a system wherein a pressure gauge removably attached to a syringe is used to monitor fluid pressure generated within the syringe, a method for maintaining the pressure gauge in a sterile condition and reusing the pressure gauge in multiple medical procedures, the method comprising the steps of:

during a first medical procedure wherein fluid pressure is generated within a first syringe, isolating said pressure gauge from contaminants, including the steps of:

using a flexible membrane in contact with a pressure transducer of said pressure gauge to communicate said fluid pressure to said pressure gauge and to prevent fluid within said first syringe from contacting said pressure gauge; and using a disposable covering extending over said pressure gauge to prevent contamination of surfaces of said pressure gauge;

after said first medical procedure, removing said pressure gauge from said first syringe;

removing said disposable covering from said pressure gauge;

without sterilizing said pressure gauge, attaching said pressure gauge to a second syringe; and monitoring fluid pressure generated in said second syringe during a second medical procedure using said pressure gauge.

20. A method as defined in claim 19, further comprising the step of applying a second disposable covering to said pressure gauge before the step of monitoring fluid pressure generated in said second syringe.

21. A method as defined in claim 19, further comprising the step of preventing fluid within said second syringe from contacting said pressure gauge during said step of monitoring fluid pressure generated in said second syringe.

22. A method as defined in claim 19, further comprising, during said first medical procedure, the step of generating fluid pressure within said first syringe.

23. A method as defined in claim 22, further comprising, during the step of generating fluid pressure within said first syringe, the step of monitoring said generated fluid pressure using said pressure gauge.

24. A method as defined in claim 22, further comprising, during the step of generating fluid pressure within said syringe, the step of inflating a balloon-tipped catheter connected to an opening at a distal end of said first syringe.

25. A method as defined in claim 19, further comprising, during said first medical procedure, the steps of:

generating within said first syringe a negative fluid pressure relative to atmospheric pressure; and monitoring said negative fluid pressure using said pressure gauge.

* * * * *

UNITED STATES PATENT AND TRADEMARK OFFICE
CERTIFICATE OF CORRECTION

PATENT NO. : 6,139,523
DATED : October 31, 2000
INVENTOR(S) : Steven R. Taylor; Arlin Dale Nelson It is certified that error appears in the above-identified patent and that said Letters Patent is hereby corrected as shown below:

Column 2,
Line 57, after "would be a" change "fixer" to -- further --

Column 5,
Line 33, after "present invention" delete "is"

Column 6,
Line 10, before "respond to" delete "be"
Line 15, before "procedures" change "medial" to -- medical --

Column 10,
Line 20, after "thin, flat" insert a comma
Line 33, after "pressure transducer" delete "in a sheet-like fashion"
Line 57, after "pressure gauge" delete "in a sheet-like fashion"

Signed and Sealed this

Fourth Day of December, 2001

*Attest:*

Nicholas P. Godici

NICHOLAS P. GODICI
*Attesting Officer*  *Acting Director of the United States Patent and Trademark Office*